(12) United States Patent
Ackermann et al.

(10) Patent No.: US 8,770,482 B2
(45) Date of Patent: Jul. 8, 2014

(54) APPARATUS AND METHOD TO ADMINISTER AND MANAGE AN INTELLIGENT BASE UNIT FOR A HANDHELD MEDICAL DEVICE

(75) Inventors: Friedrich Ackermann, Heidelberg (DE); Blaine Edward Ramey, Indianapolis, IN (US); Robert P. Sabo, Indianapolis, IN (US); Manfred Augstein, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 2485 days.

(21) Appl. No.: 11/411,723

(22) Filed: Apr. 26, 2006

(65) Prior Publication Data

US 2007/0255114 A1    Nov. 1, 2007

(51) Int. Cl.
*G06K 7/00* (2006.01)

(52) U.S. Cl.
USPC ............ 235/439; 235/435; 235/449; 235/451

(58) Field of Classification Search
USPC .............................. 702/62; 235/439, 449, 451
See application file for complete search history.

(56) References Cited

U.S. PATENT DOCUMENTS

| | | | |
|---|---|---|---|
| 5,739,665 A | | 4/1998 | Bares |
| 5,808,285 A | | 9/1998 | Rockstein et al. |
| 5,949,408 A | * | 9/1999 | Kang et al. .................... 345/169 |
| 6,102,284 A | | 8/2000 | Myers et al. |
| 6,115,248 A | * | 9/2000 | Canova et al. ............ 361/679.56 |
| 6,175,752 B1 | * | 1/2001 | Say et al. ....................... 600/345 |
| 6,283,777 B1 | | 9/2001 | Canova et al. |
| 6,407,915 B1 | | 6/2002 | Derocher et al. |
| 6,493,220 B1 | | 12/2002 | Clark |
| 6,526,092 B1 | | 2/2003 | Nelson et al. |
| 6,641,533 B2 | * | 11/2003 | Causey et al. ................. 600/300 |
| 6,648,661 B1 | | 11/2003 | Byrne et al. |
| 6,849,237 B2 | * | 2/2005 | Housefield et al. ........ 422/82.01 |
| 6,900,980 B2 | | 5/2005 | Christopher |
| 7,077,328 B2 | * | 7/2006 | Krishnaswamy et al. ......................... 235/472.01 |
| 2002/0086703 A1 | * | 7/2002 | Dimenstein et al. .......... 455/557 |

(Continued)

FOREIGN PATENT DOCUMENTS

| | | |
|---|---|---|
| GB | 2389316 A | 12/2003 |
| JP | 04-345346 | 1/1992 |

(Continued)

OTHER PUBLICATIONS

Webster's Ninth New Collegiate Dictionary principal copyright 1983, p. 1121, definition of Software.

(Continued)

*Primary Examiner* — Michael G Lee
*Assistant Examiner* — Tabitha Chedekel
(74) *Attorney, Agent, or Firm* — Dinsmore & Shohl LLP

(57) ABSTRACT

Apparatuses and methods thereof to administer and manage a base unit for a handheld medical device are disclosed. In one embodiment, a base unit of the invention is in communication with a handheld medical device. The base unit is configured to provide an electrical connection to a power source to charge a battery of the handheld medical device. The base unit is also configured to perform an update to the operation of the base unit, wherein the update is initiated by the base unit upon receiving from the handheld medical device a data stream with information indicating that an update is contained in the data stream.

81 Claims, 6 Drawing Sheets

(56) References Cited

U.S. PATENT DOCUMENTS

| | | |
|---|---|---|
| 2002/0193679 A1* | 12/2002 | Malave et al. ............ 600/407 |
| 2003/0120849 A1 | 6/2003 | Roslak et al. |
| 2003/0149317 A1 | 8/2003 | Rending |
| 2003/0149818 A1 | 8/2003 | Scott et al. |
| 2003/0149822 A1 | 8/2003 | Scott et al. |
| 2003/0172217 A1 | 9/2003 | Scott et al. |
| 2003/0172218 A1 | 9/2003 | Scott et al. |
| 2003/0191877 A1 | 10/2003 | Zaudtke et al. |
| 2004/0049233 A1 | 3/2004 | Edwards |
| 2004/0131133 A1 | 7/2004 | Charney et al. |
| 2004/0174338 A1 | 9/2004 | Scott |
| 2004/0189602 A1 | 9/2004 | Scott et al. |
| 2005/0013103 A1 | 1/2005 | Chandley |
| 2006/0166629 A1* | 7/2006 | Reggiardo ............ 455/120 |
| 2006/0253638 A1* | 11/2006 | Oliver et al. ............ 710/303 |

FOREIGN PATENT DOCUMENTS

| | | |
|---|---|---|
| JP | 04-315204 | 11/1992 |
| WO | 99/23597 | 5/1999 |
| WO | 01/69514 A2 | 9/2001 |
| WO | 2004/024232 A1 | 3/2004 |

OTHER PUBLICATIONS

McGraw-Hill Dictionary of Scientific and Technical Terms, Sixth Edition, Copyright 2003, p. 1967, definition of Software.

Accu-Check Smart Printer Manual, 4th Revision, May 7, 2002, Roche Diagnostics GmbH, 50 pages.

European Search Report, dated Aug. 21, 2007, p. 1-6.

* cited by examiner

APPARATUS AND METHOD TO ADMINISTER AND MANAGE AN INTELLIGENT BASE UNIT FOR A HANDHELD MEDICAL DEVICE

BACKGROUND OF THE INVENTION

The present invention is related to handheld medical devices, and in particular to an apparatus and method thereof to administer and manage an intelligent base unit for a handheld medical device.

Several prior art point of care (POC) systems include base units, cradles, or docking stations which provide a stable placement and position for a handheld medical device. The base units also provide a communication layer to allow the associated handheld medical device to communicate with a computer system or other information technology devices, and for charging a battery of the handheld medical device. Historically, the base units for such POC systems have served as "dumb" pass-through terminals, controlled only by hardware. For improved flexibility and better system integration, there is an increasing need for such POC systems to have base units with built-in intelligence, i.e. a micro-controller and a control flow provided in some sort of embedded firmware.

However, along with having a microcontroller and embedded firmware, comes the need to administer and manage the base units much as the handheld medical devices itself. Examples of these administrative needs include, for example, setting of configuration items by the user and firmware upgrades, wherein such prior art base units become slaved to a remote computer system in order to perform these administrative needs. One problem associated with making the base unit a slave to the remote computer system is that the point in time when an update happens may be totally inadequate. Typically, the remote computer, such as a central managing database server, is unaware of the individual circumstances in a distributed setting.

It has to be kept in mind that in order to reduce complexity and costs, the base units typically do not feature a user interface, i.e. a display or means for user input such as buttons. Without forgiving these cost advantages and adding back means for user I/O, a base unit can not be configured and administered directly (as it would be done with the POC instrument itself, for example).

SUMMARY OF THE INVENTION

It is against the above background that the inventors have recognized the need for an "intelligent base unit" as described in this application. The inventors have recognized that in addition to the computer system described above, the handheld medical device, such as a blood glucose meter, may serve as a master to administer and manage the intelligent base unit. Such active control of the administering and managing processes of the intelligent base unit provides improvements over the prior art POC systems in that the individual circumstances of the base unit can be considered before providing an update in order to meet quality, reliability, and product safety requirements.

In addition, among the many advantageous and advances, for example, the present invention reduces the complexity and manufacturing of the intelligent base unit. The present invention takes advantage of the fact that with the typically daily communication flow, the handheld medical device itself gets connected to some host via the base unit. As such, for the purpose of administration and managing the base unit, the handheld medical device takes over control of the base unit. In this manner, is it assumed that the user instructing the updates to the base unit is physically close, thereby preventing the base unit to be used otherwise and which further allows the user to control the administrative process. These assumptions significantly simplify the design of such a base unit.

In one embodiment, a method providing a handheld medical device and a base unit in communication with the handheld medical device is disclosed. The base unit is configured to provide an electrical connection to a power source to charge a battery of the handheld medical device. The method includes performing an update to the operation of the base unit, wherein the update is initiated by the base unit upon receiving from the handheld medical device a data stream with information indicating that an update is contained in the data stream.

In another embodiment, a method providing a base unit and a handheld medical device which communicates and electrically interfaces with the base unit is disclosed. The method includes receiving with the handheld medical device an update provided via the base unit, in which the base unit ignores the update. The method also includes communicating the update to the base unit from the handheld medical device in a data stream, in which the handheld medical device adds additional information to the data stream, and receiving the data stream with the base unit, wherein the base unit does not ignore the update due to detecting the additional information.

In still another embodiment, a method of administering and managing a system is disclosed. The method comprises providing a requesting unit in two-way communication with a handheld medical device via a base unit, transmitting from the requesting unit an interrogation for device data from the handheld medical device, and conveying via the base unit the interrogation to the handheld medical device. The method also includes transmitting the device data from the handheld medical device via the base unit to the requesting unit, the device data containing status information pertaining to the handheld medical device and the base unit. The method further comprises checking the status information to see if an update to the software or firmware of the handheld medical device or base unit is needed; and sending an update from the requesting unit to the handheld medical device via the base unit when needed.

In yet another embodiment, an apparatus is disclosed. The apparatus comprises a handheld medical device having a microprocessor, a first communication interface, and a battery powering the handheld medical device. A base unit having an electrical connection configured to provide power from a power source to charge the battery of the handheld medical device is also provided. The base unit also includes a second communication interface configured to communicate with the first communication interface of the handheld medical device, and a microcontroller configured to perform an update to the operation of the base unit. The update is initiated by the base unit upon receiving from the handheld medical device, via the first and second communication interfaces, a data stream with information indicating that the update is contained in the data stream.

These and other features and advantages of the invention will be more fully understood from the following description of various embodiments of the invention taken together with the accompanying drawings.

DETAIL DESCRIPTION

Figure 1B:
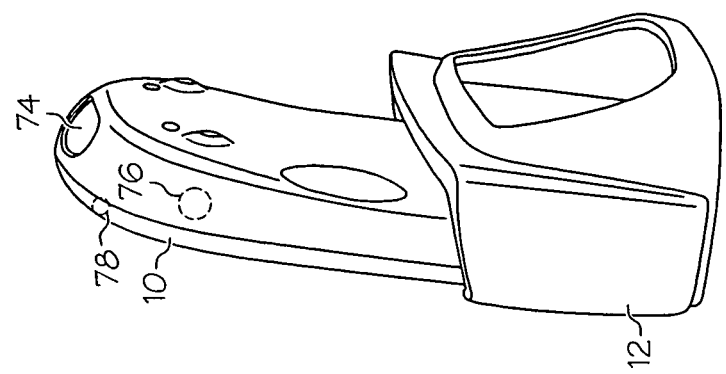
FIGS. 1A and 1B are perspective front and rear facing views, respectively, of a base unit and a handheld medical device according to an embodiment of the invention.
Figure 1A:
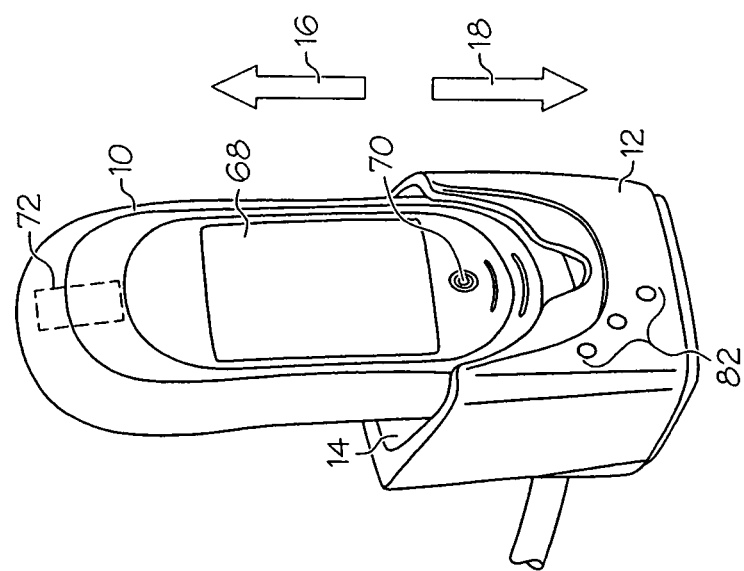
Figure 2:
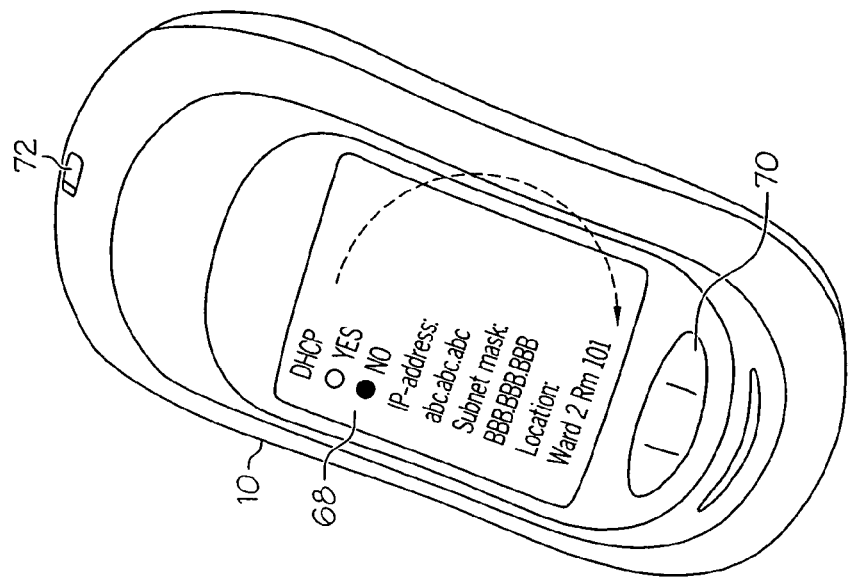
FIG. 2 is a perspective drawing of a handheld medical device administering to a base unit according to an embodiment of the invention.
Figure 2:
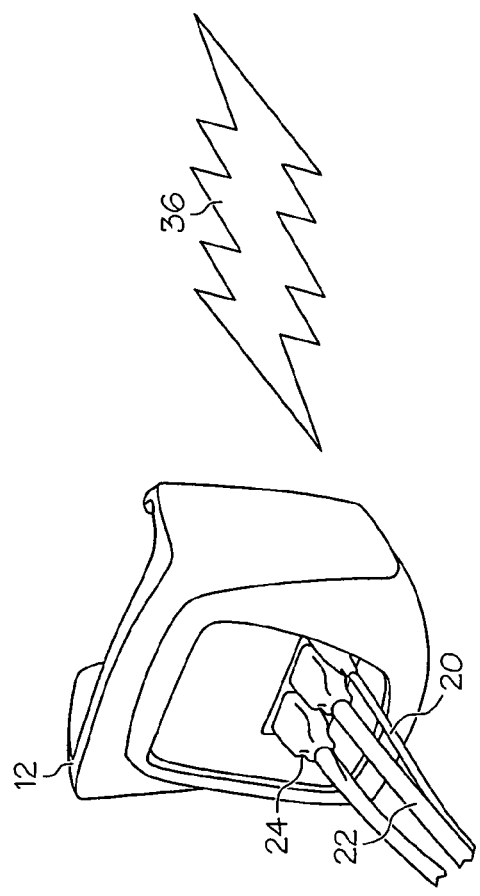
Figure 3:
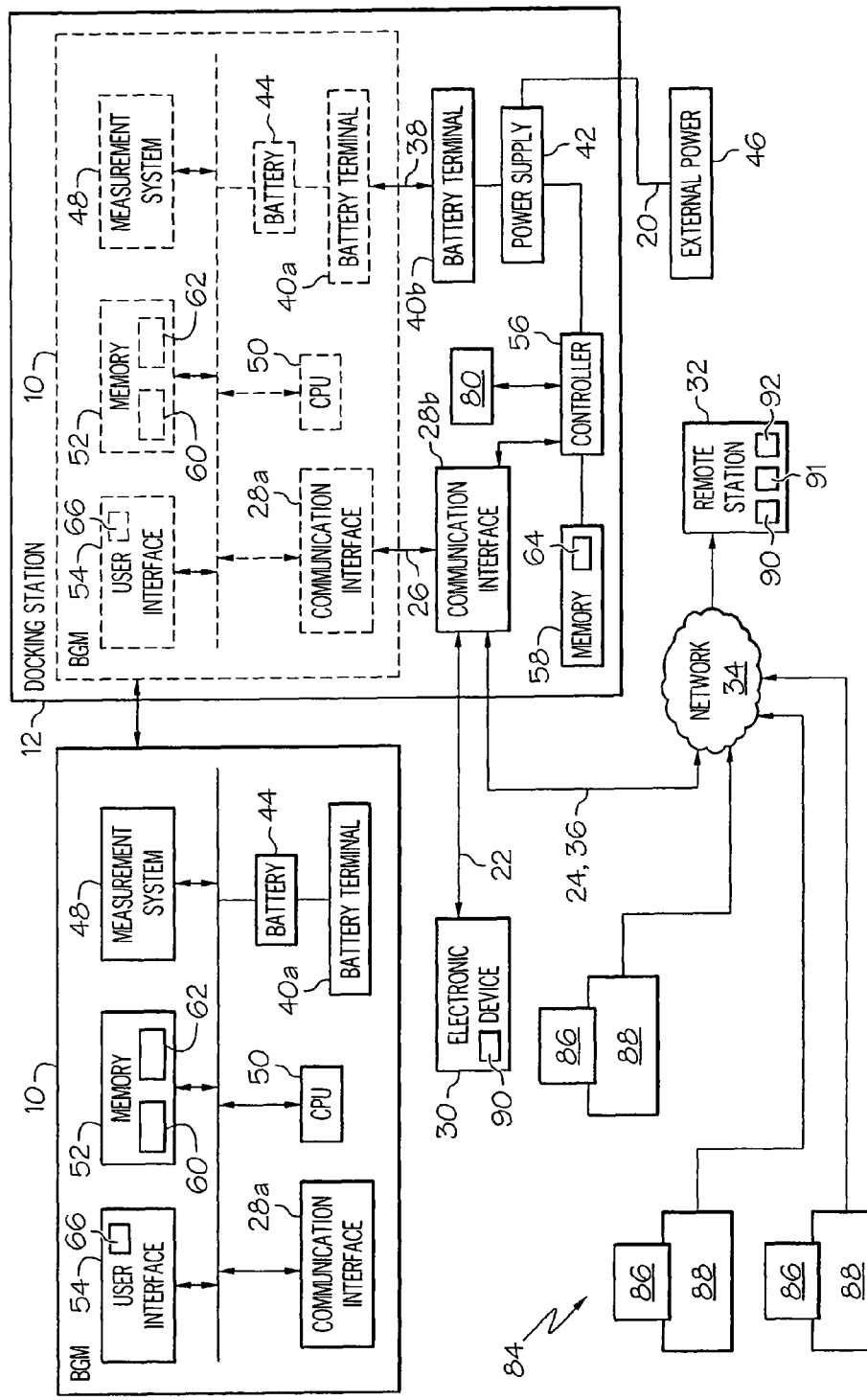
FIG. 3 is a block diagram illustrating a system for administering and managing a plurality of handheld medical devices, such as blood glucose meters (BGMs), according to an embodiment of the invention.

Referring to FIGS. 1-3, an example of one type of a handheld medical device, a hospital blood glucose meter (BGM) 10, and a base unit 12 are disclosed. The base unit 12 comprises a cradle 14 that receives the BGM 10. When an operator needs to use the BGM 10, the operator lifts the BGM 10 from the cradle 14 as illustrated by arrow 16 shown in FIG. 1. The BGM 10 is docked or returned to the cradle 14 as illustrated by arrow 18.

The base unit 14 includes a power cord 20, a port connection 22, and a network connection 24, which is illustrated in FIG. 2. The power cord 20 provides power from an external power supply for charging the BGM 10. The port connection 22 in one embodiment is a USB connection, but may be any other type of port connection, such as for example, Firewire, serial, or parallel. The network connection 24 in one embodiment is Ethernet compatible for TCP/IP-communication, and in other embodiments may be compatible with any other type of network protocol.

As shown in FIG. 3, docking the BGM 10 in the cradle 14 provides an electrical connection 26 between communication interfaces 28a and 28b of the BGM 10 and the base unit 12, respectively. Electrically connecting communication interfaces 28a and 28b provides two-way communications between the BGM 10 and an electronic device 30 via port connection 22 to base unit 12. Electrically connecting communication interfaces 28a and 28b also provides two-way communications between the BGM 10 and a remote station 32 over network 34 via network connection 24 to base unit 12.

The electronic device 30 and remote station 32 may be any type of computer, including laptops, pagers, personal digital assistants (PDAs), computer systems, computer servers, printers, mobile phones, and any medical devices or electronic devices having an embedded microprocessor running software compatible with the BGM 10 and base unit 12 and in communication with the base unit 12. Electronic device 30, since connected to the base unit 12 via port connection 22, typically will be located at the same physical location (i.e., same room) as the base unit 12. The remote station 32, since connected to the base unit 12 via network connection 24 to network 34, may be located anywhere network 34 provides a network connection 24, which also may be at the same physical location as the base unit 12.

Network 34 may be any network. Network 34 may comprise, for example, a public switched telephone network, a cellular telephone network, a local area network, a wide area network, a global computer network such as the Internet, an integrated services digital network, or the like. In some settings in which the BGM 10 and the base unit 12 may be deployed, the setting may include a dedicated security network or a private building maintenance network. Either may serve as network 34. Network 34 may include hard-wired electrical or optical communication links, wireless links, or a combination of both.

Electrically connecting communication interfaces 28a and 28b also provides two-way communications between the BGM 10 and the base unit 12 via a physical communication link. When base unit 12 receives BGM 10, mating electrical or optical components in base unit 12 and BGM 10 may engage, thereby enabling communication.

In another embodiment, the communication interfaces 28a and 28b may provide a wireless connection 36 for two-way communications between the BGM 10 and the base unit 12, which is illustrated by FIG. 2. Communication between the BGM 10 and base unit 12 may be in accordance with one or more wireless communication links, such as, for example, radio frequency, capacitive, inductive, and infrared links, employing a suitable communication protocol. For example, one communication protocol, commonly referred to as Bluetooth, uses short-range radio technology employed to transport data between devices. Other possible communication protocols include IEEE 802.11a, 802.11b, and 802.11g, and any proprietary wireless communication layers in the (Industrial, Scientific and Medical) ISM-band. Still other possible protocols are IrDA, SIR (Serial Ir), or any other optical protocol.

In addition, BGM 10 and base unit 12 may communicate via a combination of wireless and physical communication links. Wireless links and physical communication links both may be implemented so that BGM 10 may be quickly and easily removed from base unit 12 without hindrance. In such an embodiment, the base unit 12 is a wireless access node for the BGM 10, such that two-way communications between the BGM 10 and the electronic device 30, and the BGM 10 and the remote computer 32 are provided.

Seating the BGM 10 in the cradle 14 also provides an electrical connection 38 between battery terminals 40a and 40b of the BGM 10 and the base unit 12, respectively. The electrical connection between the BGM 10 and base unit 12 may be a physical connection or an inductive coupling. Electrically connecting battery terminals 40a and 40b provides electrical power from a power supply 42 of the base unit 12 to a battery 44 of the BGM 10 for charging. The power supply 42 is connected to external power supply 46 via power cord 20.

Battery 44 powers the components of the BGM 10, such as the communication interface 28a, a measurement system 48, a microprocessor 50, memory 52, and user interface 54. Power supply 42 powers the components of the base unit 12, such as the communication interface 28b, a microcontroller 56, and memory 58.

The measurement system 48 measures glucose in a blood sample of the patient, and provides output used to monitor blood glucose levels of the patient. The microprocessor 50 controls various functions of BGM 10. For example, the microprocessor 50 executes commands inputted by a user, governs charging of the battery 44, and evaluates the output from the measurement system 48 to provide information to the user, via the user interface 54, regarding the measured blood glucose level(s) of the patient. The microprocessor 50 further reads and writes to memory 52, communicates with electronic device 30 and/or remote station 32, executes a routine that performs a self-diagnostic routine 60 of BGM 10, and acquires BGM status information as a function of performing the self-diagnostic routine. The microprocessor 50 further interrogates for Base Unit (BU) status information of the base unit 12, and acquires BU status information as a function interrogating the base unit. The interrogation of the microprocessor 50 is further explained in a later section hereafter in reference to FIGS. 4 and 5.

BGM status information pertains to the operating status of the BGM 10 and its attendant components. BGM status information may include, for example, data indicative of the BGM 10 being in good working order. BGM status information may also include data indicative of a fault or potential problem with the BGM 10, such as data indicative of a failed or damaged component. Data indicating that the battery 44 is low, or that the battery is failing to hold a charge, are additional examples of BGM status information. BGM status information may also include data indicating that the serial number of the BGM, the physical location of the BGM, the communication settings of the communication interface 28*a* of the BGM, and the current software and/or firmware (FW) versions stored in memory 52. As mentioned herein, communication settings include definition of the meter's own static IP-address, definition of the meter's IP-subnet mask, and definition of timeouts or various other parameters that influence the host communication.

It is to be appreciated that the self-diagnostic routine 60 monitors the status of BGM 10. The self-diagnostic routine 60 may be performed routinely by the microprocessor 50, such as at power on, or at any other time or according to a trigger event, such as being undocked and/or docked to the base unit 12, or at the request of the user. The self-diagnostic routine 60 may be also initiated by an interrogation from either electronic device 30 or remote station 32, or may be initiated in response to a change in the condition of BGM 10, such as a component malfunction.

By execution of the self-diagnostic routine 60, the processor 50 performs one or more internal self-tests to acquire status information about the state of readiness of BGM 10. The self-diagnostic routine 60 may evaluate and identify matters that can be customer serviceable, such as software or firmware updating, and matters that may require a professional service call. The BGM status information resulting from the self-diagnostic routine 60 is stored in a data file 62, which is held in memory 52, and may present some or all of the status information via the user interface 54. When the results of the self-tests indicate that BGM 10 is ready for use, for example, user interface 54 may provide a visible or audible indication of readiness. In addition, upon request and/or after execution of the self-diagnostic routine 60, the data file 62 or select information provided therein may be provided to the electronic device 30, the remote station 32, and/or another BGM.

The microcontroller 56 controls various other functions of base unit 12. For example, the microcontroller 56 monitors and governs supplying power to the battery terminal 40*b* from power supply 42, and will disconnect such power should a fault condition be detected. The microcontroller 56 further reads and writes to memory 58, and communicates with the BGM 10 via communication interface 28*b*. Upon receiving an interrogation from the BGM 10, via the communication interface 28*b*, the microcontroller 56 executes a routine from memory 58 that performs a self-diagnostic test 64 of base unit 12.

It is to be appreciated that the self-diagnostic test 64 monitors the status of base unit 12. The self-diagnostic test 64 may be initiated by the microcontroller 56, by receiving an interrogation from the BGM 10, or may be initiated in response to a change in the condition of base unit 12. Self-diagnostic test 64 may evaluate and identify matters that can be customer serviceable and matters that may require a professional service call. In one embodiment, the base unit 12 transmits BU status information to the BGM 10 and applies received updates as a function of performing the self-diagnostic test 64. The microcontroller 56 may also execute additional commands inputted by a user via the BGM 10, such as adjusting configuration settings, reporting usage events, serial information, and accepting location information, for example.

BU status information pertains to the operating status of the base unit 12 and its attendant components. BU status information may include, for example, data indicative of the base unit 12 being in good working order. BU status information may also include data indicative of a fault or potential problem with the base unit 12, such as data indicative of a failed or damaged component. Data indicating that the serial number of the base unit, the physical location of the base unit, the communication settings of the communication interface 28*b*, the number of docking events for usage/wear metering, and the current software and/or firmware (FW) version of the base unit are additional examples of BU status information. As mentioned herein, communication settings include definition of the base unit's own static IP-address, definition of the base unit's IP-subnet mask, and definition of timeouts or various other parameters that influence the host communication. As with the BGM status information, the BU status information is recorded in the data file 62 of the BGM 10.

The user interface 54 of the BGM 10 may include one or more input/output elements 66 that convey status information to the user. The input/output elements 66 also convey testing information to the user, such as part of a blood glucose testing procedure being performed by the BGM 10. As shown in FIGS. 1A, 1B and 2, input/output elements 66 include a touch screen display 68, a selector button 70, a test reader 72, and an optical reader 74. It is to be appreciated that test reader 72 enables the reading of a test carrier, such as, for example, a strip, a cassette, a cartridge or any other suitable test carrier. Input/output elements 66 may include other or additional elements, such as for example, a speaker 76 that is capable of delivering an audible signal or a spoken message, and a microphone 78 for receiving audible commands from the user.

In one illustrated embodiment, FIG. 2 indicates how the BGM 10 is used in order to administer the base unit 12. BGM 10 wirelessly communicates with the base unit 12 as shown via a wireless connection such as IrDA. The user holds the BGM 10 and directs a communication interface towards the base unit 12. Alternately, the BGM 10 may be docked in the base unit 12 such that IrDa windows in both devices align while performing this activity. The user then retrieves BU status information, and/or determines and provides all communication and operating setting of the base unit 12 using the input/output elements 66 of the BGM 10. In particular, the touch screen display 68 of the BGM 10 shows an illustrative screen shot. In one embodiment, the touch screen display 68 of the BGM 10 is provided with an option to present displayed content turned by 180 degrees. Such an option is useful in situations where the user would keep the BGM 10 in hand for the above programming activity, but in a different orientation than in the course of the usual workflow of the meter performing blood glucose monitoring.

The touch screen display 68 may convey, for example, that the BGM 10 and the base unit 12 are in good working order, or that the communication interfaces of the BGM 10 and the base unit 12 are working properly. The touch screen display 68 also may accept input from the user, and convey any information in text or visual form, such as pictorial instructions, or a text warning that the BGM 10 is out of service, along with directions for finding the nearest BGM in the network that is in service. Selector button 70 may turn the BGM 10 on or off, permit the user to select from a menu of displayed choices, and accept commands from the user. The test reader 72 and the optical reader 74 (e.g., for barcodes, hand recognition, pattern recognition, optical character recognition, optical mark recognition, and combinations thereof) (FIG. 1A) are used as part of inputting data needed to conduct the testing of the glucose level of the patient. The speaker 76 may convey, for example, an alarm signaling that the BGM 10 is not properly seated in the base unit, or verbal instructions concerning use of BGM 10 or base unit 12.

Referring back to FIG. 3, base unit 12 also includes output elements 80 that may be redundant of input/output elements 66 on BGM 10. In other words, output elements 80 of base unit 12 may convey the same status information as output elements 66 of BGM 10. Output elements 80 may also convey BU status information in a different way than that conveyed by BGM 10. Base unit 12 may, for example, employ a simplified visual indicator system 82 (FIG. 1A), while BGM output elements 66 may be more specific about the nature of any problems. The visual indicator system 82 may comprise, for example, light-emitting diodes (LEDs) that illuminate or darken to convey status information. The visual indicator system 82 may, for example, indicate whether the base unit 12 is in good working order, the network connection is good, the port connection is good, data is being transmitted or received over the port connection and the network connection, and whether the base unit needs service.

The BGM 10 and the base unit 12 may be part of a networked system 84 of handheld medical devices 86 and their associated base unit 88, wherein in one embodiment devices 86 and base units 88 are other BGMs 10 and base units 12. In one embodiment, the status information conveyed by the BGM 10 and base unit 12 may include status information pertaining to the networked system 84. Other devices 86 may communicate with remote station 32 via network 34. In particular, remote station 32 may receive status information from BGM 10 and devices 86 regarding a particular device and the associated base unit in system 84. Remote station 32 may also transmit interrogations and updates to any or all devices 10, 86 in system 84.

Remote station 32 provides a central point for monitoring, collecting, and aggregating status information pertaining to the devices and their associated base units in system 84. The remote station 32 may summarize the aggregated status information and present the status information via an input/output device 90. Input/output device 90 may comprise one or more display screens, keyboards, audible alarms, LEDs, LCDs, printers, touch screens, pointing devices, and the like. Input/output device 90 may also comprise a communication device 91 configured to establish a communication link with another person or device not shown in FIG. 3.

For example, when status information from any of the devices 10, 86 indicates at problem that may require a professional service call, the remote station 32 may automatically summon the service provider via input/output device 90. In addition, when analysis by the remote station 32 of received status information from any of the devices 10, 86 indicates that a version of the software or firmware employed by a device and/or associated base unit requires updating, the remote station 32 may automatically transmit the required update to the device via input/output device 90 and network 34. The remote station 32 may further store information pertaining to the status of system 84, or any device 10, 86 or base units 12, 88 in system 84, in memory 92. Information stored in memory 92 may include, for example, routine status information, software and firmware version numbers, data pertaining to repair histories, and tracking data showing the locations and usage of the devices 10, 86 and base units 12, 88.

In one illustrative embodiment, a personal computer may operate as remote station 32 having input/output device 90, communication device 91, and memory 92. In another illustrative embodiment, a portable device such as a cell phone, pager, or personal digital assistant (PDA) may operate as the input/output device 90, with remote station 32 and memory 92 located in a different physical location. In this embodiment, remote station 32 and input/output device 90 may communicate via a communication link such as a wireless link or a telephone line, via communication device 91. Remote station 32 and input/output device 90 may also communicate over network 34.

A responsible person, such as a network supervisor, may observe the status of any device 10, 86 or base unit 12, 88 in system 84 by observing input/output device 90. Input/output device 90 may notify the responsible person that all devices 10, 86 and base units 12, 88 in system 84 are operational, for example, or may notify the responsible person when a device or a base unit in system 84 is in need of attention. When a device 10, 86 or a base unit 12, 88 in system 84 is in need of attention, input/output device 90 may present the responsible person with information such as the location of the device in question and the nature of the problem. Input/output device 90 may further present the responsible person with status information received from the device 10, 86 in response to an interrogation by remote system 32. Input/output device 90 may also present the responsible person with data stored in memory 92, such as the repair history of the device in question.

Figure 4:
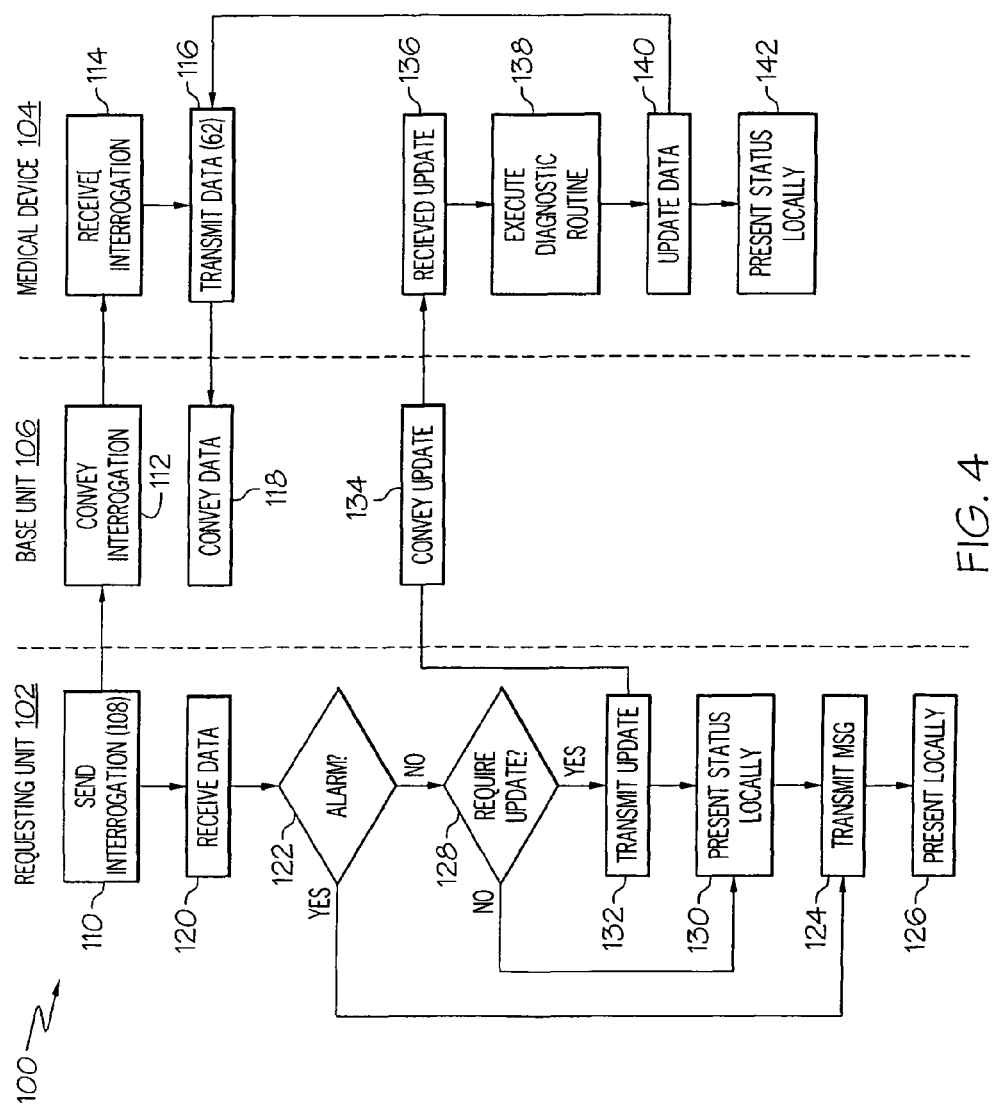
FIG. 4 is a flow diagram illustrating interrogation of a handheld medical device according to an embodiment of the invention.
Figure 5:
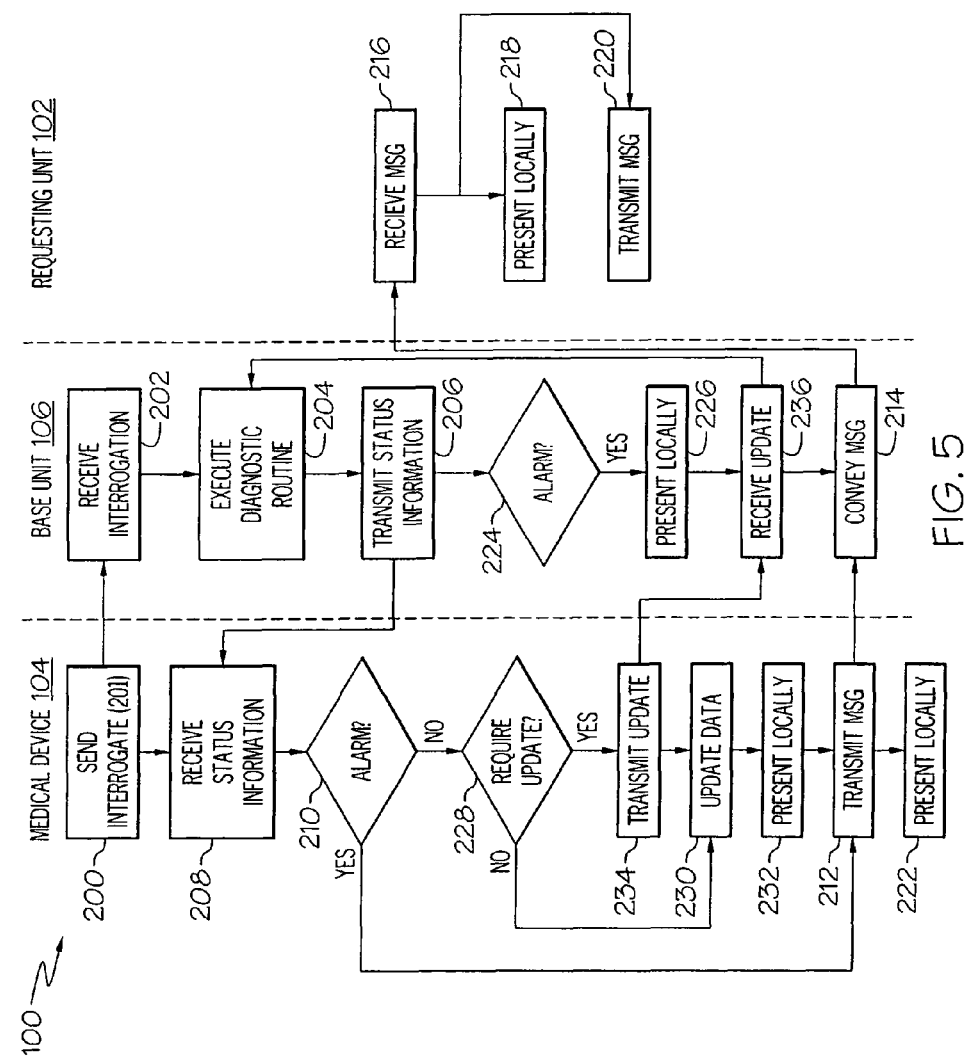
FIG. 5 is a flow diagram illustrating interrogation of a base unit by a handheld medical device according to an embodiment of the invention.
Figure 6:
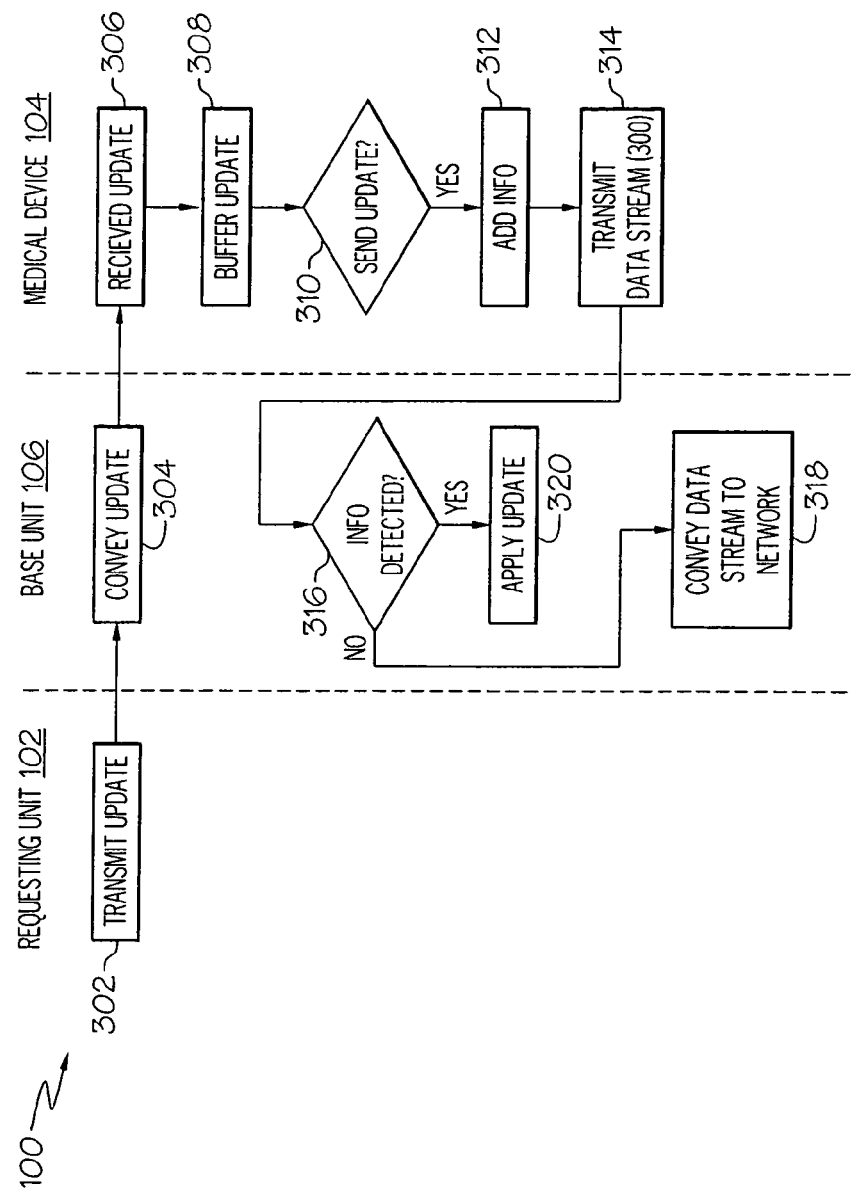
FIG. 6 is a flow diagram illustrating updating of a base unit via active control from a handheld medical device according to an embodiment of the invention.

FIGS. 4-6 are flow diagrams illustrating embodiments of a system 100 in which either an electronic device or remote station interrogates for and receives status information from a handheld medical device and a base unit, and provides updates. System 100, electronic device, remote station, handheld medical device, and base unit may be the embodiments depicted in FIGS. 1-3, but are not limited to those embodiments.

In the embodiment of system 100 shown in FIG. 4, a requesting unit 102, which may be either electronic device 30, remote station 32, or device 86, is in two-way communication with handheld medical device 104 via base unit 106. In operation, an interrogation 108 for status information is transmitted from the requesting unit 102 to handheld medical device 104 in step 110. In step 112, the base unit 106 conveys the interrogation to the handheld medical device 104, which is received in step 114. In step 116, the handheld medical device 104 will transmit device data 62, such as a device log or any other type of data recording and reporting method, to the requesting unit 102, which is conveyed by the base unit 106 in step 118.

In step 120, the requesting unit 102 receives the device data 62, and processes the status information contained therein in step 122 for an alarm or service condition, which requires a responsible person to physically attend to the responding handheld medical device 104. If such an alarm or service condition exists, then in step 124 the requesting unit 102 may send a message to another device indicating the alarm or service condition and location of the handheld medical device 104. Additionally, such information may be presented locally, such as via input/output device 90 (FIG. 3), in step 126. If no alarm or service condition exists, then in step 128, the requesting unit 102 checks to see if an update to the software or firmware of the handheld medical device 104 is needed. If in an update is not required, then in step 130 the status information may be presented locally on the requesting unit 102, such as by input/output device 90 (FIG. 3). If an update is required, then in step 132, the update is transmitted from the requesting unit 102 to the handheld medical device 104. In step 134, the base unit 106 conveys the update to the handheld medical device 104.

After receiving the update in step 136, the handheld medical device 104 in step 138 performs a self-diagnostic routine, such as routine 60 (FIG. 3), to apply the update and acquire new status information. In step 140, the handheld medical device 104 updates the device data with the newly acquired status information. The handheld medical device 104 then repeats step 116 to communicate the device data, via the base unit 106, to the requesting unit 102. The requesting unit 102 then repeats at least step 128 to determine if repeating the remaining process steps described above is needed. In step 142, the status information from the updated device data may be presented on the handheld medical device 104, such as by user interface 54 (FIG. 3).

Handheld medical device 104 may further communicate the status information of the base unit 106 to the requesting unit 102. However, it is to be appreciated that in system 84, neither the electronic device 30 nor the remote station 32 (FIG. 3) interrogates the base unit 106 for status information directly. Rather, as shown by FIG. 5, the handheld medical device 104 interrogates the base unit 106 for status information in step 200. The interrogation 201 from the handheld medical device 104 in step 200 may be initiated as part of the diagnostic routine, such as executed in step 138 (FIG. 4), when so commanded by a user of the handheld medical device 104, such as via the user interface 54 (FIG. 3), or according to a triggering event, such as power on, change in an operating condition, or after a designated period of time.

After the base unit 106 receives the interrogation in step 202, a diagnostic routine, such as routine 64 (FIG. 3), is executed by the base unit in step 204. The base unit 106 then transmits the BU status information to the handheld medical device 104 in step 206, which is received in step 208. In step 210, the handheld medical device 104 processes the status information received in step 208 for an alarm or service condition, which requires a responsible person to physically attend to the base unit 106. If such an alarm or service condition exists, then in step 212 the handheld medical device 104 may send a message to another device, such as remote station 32 (FIG. 3), indicating the alarm or service condition and location of the base unit 106. For example, if network connectivity is still available, such a message is conveyed via the base unit 106 from the handheld medical device 104 to a designated unit, such as for example, requesting unit 102 in step 214, which is received in step 216, and displayed locally on the requesting unit 102 in step 218. The requesting unit 102 may send a further message to a designated responsible person(s), such as via communication device 91 or network 34 (FIG. 3), regarding the alarm or service condition in step 220.

Additionally, such an alarm or service message may be presented locally on the handheld medical device 104, such as via input/output device 68 (FIG. 2), in step 222. In the embodiment where the base unit is provided with visual indicators, such as status indicators 82 (FIG. 1A), then in step 224, the base unit 106 checks to see if an alarm or service condition exists, and if so then in step 226, an indication of the alarm or service condition is provided, such as via status indicators 82.

In step 228, the handheld medical device 104 checks to see if an update to the software or firmware of the base unit 106 is needed. If an update is not required, then in step 230 the device data is updated with the received BU status information, which may be presented locally, such as by input/output device 90 (FIG. 3), in step 232. If an update is required, then in step 234, the update is transmitted from memory of the handheld medical device 104 to the base unit 106. In step 236, the base unit 106 receives the update. After receiving the update, the base unit 106 performs the self-diagnostic routine as mentioned in step 204, such as routine 64 (FIG. 3), to apply the update and acquire new status information, repeating the remaining processing thereafter mentioned above. In one embodiment, the update may include programming the base unit 106 with the network settings required and sent by the handheld medical device 104.

In another embodiment depicted by FIG. 6, the requesting unit 102, such as remote station 32 (FIG. 3), can issue software or firmware updates to the base unit 106 in system 100. In this embodiment, the requesting unit 102 sends an update in step 302, which is conveyed via the base unit 106 in step 304, and received by the handheld medical device 104 in step 306. In step 308, the receiving handheld medical device 104 buffers the update in memory. In step 310, the handheld medical device 104 sends the update at an appropriate time. It is to be appreciated that the appropriate time may be according to a triggering event, such as step 226 (FIG. 5) or determined by a user operating the handheld medical device 104.

Next, before sending the update to the base unit 106, in step 312, the handheld medical device 104 adds information, such as a protocol header to data stream 300 containing the update. It is to be appreciated that adding the information, such as the preceding protocol header, allows the base unit 106 to recognize that it shall not ignore the content in the data stream following the protocol header, but rather to handle it as an upgrade. Otherwise, the base unit 106 would ignore the content of the data stream 300, as with all communications between network devices and the handheld medical device 104, when the additional information, such as the protocol header, is not provided in the data stream. For example, in step 314, the protocol header and update is sent from the handheld medical device 104 to the base unit 106, which in step 316 checks the data stream 300 for the protocol header. If in the case that the protocol header is not detected, then data stream would be conveyed in step 318 to the network for handling. However, in this example, after detecting the protocol header in the data stream 300, the base unit 106 then applies the update, such as by executing a diagnostic routine, such as routine 204 (FIG. 5) in step 320. Additional steps, such as described after step 204 in regards to the system embodiment illustrated in FIG. 5, may also be performed such that the device data is updated and status information is displayed on the handheld medical device 104 locally to indicate that the update has been successfully applied.

Various embodiments of the invention have been described. These specific embodiments are illustrative of the practice of the invention. Various modifications may be made without departing from the scope of the claims. For example, the invention is not limited to blood glucose meters and their associated base units, but may be practiced with a variety of medical devices. The invention is not limited to systems in which medical devices or base units are deployed in fixed locations. In some instances, it may be beneficial to deploy a BGM and base unit in a mobile platform, such as an ambulance or a vehicle used by a security guard. Moreover, the invention includes embodiments in which the remote station is mobile.

Many examples of communication techniques are described for communication among medical devices, base units, and a remote station. The invention is not limited to the techniques explicitly described. Communication may be based upon optical communication links, magnetic communication links, infrared communication links, or visual status change detectors. Furthermore, several radio frequency communication links have been described, but the invention is not limited to the techniques explicitly described. A cellular telephone link, for example, may employ any recognized communication protocol, such as code division multiple access (CDMA), Global System for Mobile Communications (GSM), or General Packet Radio Service (GPRS).

Moreover, the invention includes software to carry out the techniques described herein. The invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software.

The instructions and the media are not necessarily associated with any particular computer or other apparatus, but may be carried out by various general-purpose or specialized machines. The instructions may be distributed among two or more media and may be executed by two or more machines. The machines may be coupled to one another directly, or may be coupled via a network.

The invention may also be embodied as one or more devices that include logic circuitry to carry out the functions or methods as described above. The logic circuitry may include a processor that may be programmable for a general purpose or may be dedicated, such as microcontroller, a microprocessor, a Digital Signal Processor (DSP), Application Specific Integrated Circuit (ASIC), and the like.

The above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

What is claimed is:

1. A method comprising:
providing a handheld medical device;
providing a base unit in communication with said handheld medical device, said base unit providing an electrical connection to a power source to charge a battery of said handheld medical device; and
performing an update to software or firmware of the base unit, wherein the update is initiated by said base unit upon receiving from the handheld medical device a data stream with information indicating that an update to the software or firmware of the base unit is contained in said data stream.

2. The method of claim 1, further comprising receiving said update by the handheld medical device via the base unit.

3. The method of claim 1, further comprising receiving said update by the handheld medical device via the base unit, wherein said update is ignored by said base unit and sent back to the base unit in the data stream from the handheld medical device with the information indicating that the update is contained in the data stream, said handheld medical device adding said information to said data stream.

4. The method of claim 1, wherein said update is performed as a part of a self-diagnostic test executed in response to a change in the operating condition of the base unit.

5. The method of claim 1, wherein said update is performed as part of a self-diagnostic test, said self-diagnostic test also evaluates status information of the base unit and identifies matters that can be customer serviceable and matters that require a professional service call.

6. The method of claim 1, wherein said update is performed as part of a self-diagnostic test, said self-diagnostic test also transmits status information on the base unit to the handheld medical device.

7. The method of claim 1, further comprising performing commands inputted by a user via the handheld medical device.

8. The method of claim 1, further comprising performing commands inputted by a user via the handheld medical device, wherein said commands include at least one of adjusting configuration settings of the base unit, reporting usage events of the base unit, serial information of the base unit, and accepting location information.

9. The method of claim 1, further comprising transmitting base unit status information to the handheld medical device, wherein the base unit status information comprises at least one of data indicative of the base unit being in good working order, data indicative of a fault or potential problem with the base unit, data indicating a serial number of the base unit, data indicating a physical location of the base unit, data indicating communication settings of the base unit, data indicating number of docking events for usage/wear metering, and data indicating current software and/or firmware versions of the base unit.

10. The method of claim 1, further comprising transmitting base unit status information to the handheld medical device, wherein the base unit status information comprises data indicating communication settings of the base unit, wherein said communication settings include at least one of definition of static IP-address of base unit, definition of IP-subnet mask of base unit, and definition of timeouts and various other parameters that influence host communication of the base unit.

11. The method of claim 1, further comprising transmitting base unit status information to the handheld medical device, wherein the base unit status information is recorded in a data file of the handheld medical device.

12. The method of claim 1, wherein the handheld medical device has a user interface that comprises at least one of a touch screen display, a selector button, a test reader, an optical reader, a speaker, a microphone, and combinations thereof.

13. The method of claim 1, wherein the handheld medical device has an option to present displayed content turned by 180 degrees on a display.

14. The method of claim 1, wherein said base unit includes output elements, and said method further comprises display operational status of the base unit on said output elements.

15. A method comprising:
providing a base unit;
providing a handheld medical device which communicates and electrically interfaces with said base unit;
receiving with said handheld medical device an update provided via said base unit, said base unit ignoring the update;
communicating said update to said base unit from said handheld medical device in a data stream, said handheld medical device adding additional information to said data stream; and
receiving said data stream with said base unit, wherein said base unit does not ignore the update due to detecting said additional information.

16. The method of claim 15, further comprises connecting said base unit to a communications network and receiving the update from the communications network.

17. The method of claim 15, wherein said handheld medical device communicates wirelessly with said base unit.

18. The method of claim 15, wherein said handheld medical device communicates with said base unit via a physical connection.

19. The method of claim 15, wherein said handheld medical device and said base unit communicate via a combination of wireless and physical communication links.

20. The method of claim 15, further comprising providing two-way communications via the base unit between the handheld medical device and at least one of an electronic device connected directly to the base unit and a remote station connected to the base unit over a network, wherein the update is provided from at least one of the electronic device and the remote station.

21. The method of claim 15 further comprising providing two-way communications via the base unit between the handheld medical device and at least one of an electronic device connected directly to the base unit and a remote station connected to the base unit over a network, wherein the update is provided from at least one of the electronic device and the remote station, and wherein the electronic device and the remote station are at least one of a computer, a laptop, a pager, a personal digital assistant, a computer server, a printer, a mobile phone, and any medical devices or electronic devices having an embedded microprocessor running software compatible with said handheld medical device and base unit and in communication with the base unit.

22. The method of claim 15 further comprising providing two-way communications via the base unit between the handheld medical device and at least one of an electronic device connected directly to the base unit and a remote station connected to the base unit over a network, wherein the update is provided from at least one of the electronic device and the remote station, and wherein said network is at least one of a public switched telephone network, a cellular telephone network, a local area network, a wide area network, a global computer network, an integrated services digital network, a dedicated security network, and a private building maintenance network.

23. The method of claim 15 further comprising providing two-way communications via the base unit between the handheld medical device and at least one of an electronic device connected directly to the base unit and a remote station connected to the base unit over a network, wherein the update is provided from at least one of the electronic device and the remote station, and wherein said network comprises at least one hard-wired electrical links, optical communication links, wireless links, and combinations thereof.

24. The method of claim 15, wherein the handheld medical device and the base unit electrically interface by an electrical connection that is at least one of a physical connection and an inductive coupling.

25. The method of claim 15, further comprising performing a self-diagnostic routine on the handheld medical device and acquiring status information as a function of performing the self-diagnostic routine.

26. The method of claim 15, further comprising performing a self-diagnostic routine on the handheld medical device and acquiring status information as a function of performing the self-diagnostic routine, wherein the status information pertains to at least one of data indicating operating status of the handheld medical device, data indicative of the handheld medical device being in good working order, data indicative of a fault or potential problem with the handheld medical device, data indicating that a battery is low, data indicating that the battery is failing to hold a charge, data indicating a serial number of the handheld medical device, data indicating a physical location of the handheld medical device, data indicating communication settings of the handheld medical device, data indicating current software and firmware versions, data indicating static IP-address of the handheld medical device, data indicating IP-subnet mask of the handheld medical device, and data indicating timeouts and various other parameters that influence communication of the handheld medical device.

27. The method of claim 15, further comprising performing a self-diagnostic routine on the handheld medical device and acquiring status information as a function of performing the self-diagnostic routine, wherein said self-diagnostic routine is performed routinely by an included microprocessor of the handheld medical device due to a triggering event, said triggering event being at least one of powering on the handheld medical device, undocking the handheld medical device from the base unit, docking the handheld medical device to the base unit, receiving an interrogation via the base unit from another electronic device, at a request of a user commanded via a user interface of the handheld medical device, and when a change in the operational condition of handheld medical device occurs.

28. The method of claim 15, further comprising performing a self-diagnostic routine on the handheld medical device and acquiring status information as a function of performing the self-diagnostic routine, wherein said self-diagnostic routine evaluates the status information and identifies matters that can be customer serviceable and matters that require a professional service call.

29. The method of claim 15, further comprising performing a self-diagnostic routine on the handheld medical device and acquiring status information as a function of performing the self-diagnostic routine, wherein said status information resulting from the self-diagnostic routine is stored in a data file, which is held in memory of the handheld medical device, and wherein said handheld medical device is configured to present at least some of the status information via a user interface.

30. The method of claim 15, further comprising performing a self-diagnostic routine on the handheld medical device and acquiring status information as a function of performing the self-diagnostic routine, and providing via said base unit at least some of said status information to a requesting unit.

31. The method of claim 15, further comprising performing a self-diagnostic routine on the handheld medical device and acquiring status information of the handheld device and base unit as a function of performing the self-diagnostic routine, and providing via said base unit at least some of said status information to a requesting unit in communication with said base unit.

32. The method of claim 15, further comprising said handheld medical device interrogating the base unit for status information, and acquiring the status information from the base unit as a function of interrogating the base unit.

33. The method of claim 15, wherein the base unit includes a microcontroller which monitors and governs supplying power to a battery terminal from a power supply, and the method further comprising disconnecting such power should a fault condition in the power supply be detected by the base unit.

34. The method of claim 15, further comprising sending an interrogation from the handheld medical device, and upon receiving the interrogation from the handheld medical device, said base unit performs a self-diagnostic test which provides status information to the handheld medical device.

35. The method of claim 15, further comprising sending an interrogation from a requesting unit in communication with the handheld medical device via the base unit, and upon receiving the interrogation from the requesting unit, said handheld medical device performs a self-diagnostic test which provides status information to the requesting unit.

36. The method of claim 15, further comprising sending an interrogation from a requesting unit in communication with the handheld medical device via the base unit, and upon receiving the interrogation from the requesting unit, said handheld medical device performs a self-diagnostic test which provides status information to the requesting unit; and sending updates from said requesting unit to said handheld medical device based on data contained in said status information.

37. The method of claim 15, further comprising sending an interrogation from a requesting unit in communication with the handheld medical device via the base unit, and upon receiving the interrogation from the requesting unit, said handheld medical device performs a self-diagnostic test which provides status information to the requesting unit, wherein said requesting unit provides a central point for monitoring, collecting, and aggregating status information pertaining to a network of a plurality of handheld medical devices and their associated base units.

38. A method of administering and managing a system, said method comprising:
providing a requesting unit in two-way communication with a handheld medical device via a base unit;
transmitting from the requesting unit an interrogation for device data from the handheld medical device;
conveying via the base unit the interrogation to the handheld medical device;
transmitting the device data from the handheld medical device via the base unit to the requesting unit, said device data containing status information pertaining to the handheld medical device and the base unit;
wherein the requesting unit checks the status information to see if an update to software or firmware of at least the base unit is needed; and
sending an update from the requesting unit to the handheld medical device via the base unit when needed.

39. The method of claim 38, further comprising performing a self-diagnostic routine after receiving the update to apply the update and acquire new status information; and updating the device data with the newly acquired status information.

40. The method of claim 38, further comprising performing a self-diagnostic routine after receiving the update to apply the update and acquire new status information; updating the device data with the newly acquired status information; and sending said updated device data to said requesting unit; and determining from the updated device data if repeating the sending of an update is needed.

41. The method of claim 38, wherein said requesting unit provides a central point for monitoring, collecting, and aggregating status information pertaining to a network of a plurality of handheld medical devices and their associated base units.

42. The method of claim 38, further comprising communicating updated device data containing newly acquired status information via the base unit to the requesting unit after applying the update.

43. The method of claim 38, further comprising communicating updated device data containing newly acquired status information via the base unit to the requesting unit; and determining from the updated device data if repeating the sending of an update is needed.

44. The method of claim 38, further comprising providing at least some of the status information to an output device.

45. The method of claim 38, further comprising processing the status information for an alarm or service condition, wherein if such an alarm or service condition exists, sending a message to another device indicating the alarm or service condition and location of the handheld medical device.

46. The method of claim 38, further comprising sending a second interrogation from the handheld medical device to said base unit for base unit status information.

47. The method of claim 38, further comprising sending a second interrogation from the handheld medical device to said base unit for base unit status information, wherein said sending the second interrogation is initiated according to a triggering event, said triggering being at least one of running a self-diagnostic routine of the handheld medical device, being commanded by a user of the handheld medical device via a user interface, powering on of the handheld medical device, detecting a change in an operating condition of the base unit, and elapsing of a designated period of time.

48. The method of claim 38, further comprising performing a self-diagnostic routine after receiving the update to apply the update and to acquire new status information; updating the device data with the newly acquired status information; and sending a second interrogation from the handheld medical device to said base unit for base unit status information, wherein the base unit after receiving the second interrogation executes a diagnostic routine, and then transmits base unit status information to the handheld medical device.

49. The method of claim 38, further comprising sending a second interrogation from the handheld medical device to said base unit for base unit status information; and receiving the base unit status information, wherein the handheld medical device processes the base unit status information for an alarm or service condition.

50. The method of claim 38, further comprising sending a second interrogation from the handheld medical device to said base unit for base unit status information; and receiving the base unit status information, wherein the handheld medical device processes the status information from the base unit for an alarm or service condition, and wherein if an alarm or service condition exists, then the handheld medical device sends a message to another device indicating the alarm or service condition.

51. The method of claim 38, further comprising sending a second interrogation from the handheld medical device to said base unit for base unit status information; and receiving the base unit status information, wherein the handheld medical device processes the base unit status information for an alarm or service condition, and wherein if an alarm or service condition exits, a message is presented on the handheld medical device.

52. The method of claim 38, further comprising sending a second interrogation from the handheld medical device to said base unit for base unit status information; and receiving the base unit status information; checking to see if a base unit update to the software or firmware of the base unit is needed, and if so required, then transmitting the base unit update from the handheld medical device to the base unit.

53. The method of claim 38, further comprising transmitting a base unit update from the handheld medical device to the base unit.

54. The method of claim 38, further comprising transmitting a base unit update from the handheld medical device to the base unit, wherein after receiving the base unit update, the base unit performs the self-diagnostic routine again to apply the update and acquire new status information.

55. The method of claim 38, further comprising transmitting a base unit update from the handheld medical device to the base unit, wherein the base unit update includes programming the base unit with network settings required by the handheld medical device.

56. An apparatus comprising:
a handheld medical device having a microprocessor, a first communication interface, and a battery powering the handheld medical device; and
a base unit having an electrical connection which provides power from a power source to charge the battery of said handheld medical device, a second communication interface which communicates with said first communication interface of the handheld medical device, and a microcontroller which performs an update to software or firmware of the base unit, wherein the handheld medical device is configured to add information to a data stream containing the update such that the base unit does not ignore the update to the software or firmware of the base unit contained in the data stream, and wherein said microcontroller of the base unit is configured to initiate the update upon receiving from the handheld medical device, via the first and second communication interfaces, the data stream with the information indicating that the update to the software or firmware of the base unit is contained in said data stream.

57. The apparatus of claim 56, further comprises a network connected to said base unit, wherein said handheld medical device is in communication with said network though said base unit, and wherein said handheld medical device is configured to receive said update from the network via the base unit.

58. The apparatus of claim 56, wherein said base unit is configured to perform commands inputted by a user via the handheld medical device.

59. The apparatus of claim 56, wherein said base unit is configured to perform commands inputted by a user via the handheld medical device, wherein said commands include at least one of adjusting communication settings of the base unit, reporting usage events of the base unit, serial information of the base unit, and accepting location information.

60. The apparatus of claim 56, wherein said base unit is configured to transmit base unit status information to the handheld medical device upon receiving an interrogation via said second communication interface, wherein the base unit status information comprises at least one of data indicative of the base unit being in good working order, data indicative of a fault or potential problem with the base unit, data indicating a serial number of the base unit, data indicating a physical location of the base unit, data indicating communication settings of the base unit, data indicating number of docking events for usage/wear metering, and data indicating current software and/or firmware versions of the base unit.

61. The apparatus of claim 56, wherein said base unit is configured to transmit base unit status information to the handheld medical device upon receiving an interrogation via said second communication interface, wherein the base unit status information comprises data indicating communication settings of the base unit, wherein said communication settings includes definition of static IP-address of base unit, definition of IP-subnet mask of base unit, and definition of timeouts and various other parameters that influence host communication of the base unit.

62. The apparatus of claim 56, wherein the handheld medical device has a user interface that comprises a touch screen display, a selector button, a test reader, an optical reader, a speaker, a microphone, and combinations thereof.

63. The apparatus of claim 56, wherein the handheld medical device is a blood glucose meter.

64. The apparatus of claim 56, wherein the handheld medical device has a touch screen display, and wherein the handheld medical device is provided with an option to present displayed content turned by 180 degrees on the touch screen display.

65. The apparatus of claim 56, wherein said base unit includes output elements.

66. The apparatus of claim 56, wherein said handheld medical device communicates wirelessly with said base unit, wherein said first and second communication interfaces are configured to use radio frequencies, capacitive links, inductive links, infrared links, and combinations thereof.

67. The apparatus of claim 56, wherein said handheld medical device communicates with said base unit via a physical connection.

68. The apparatus of claim 56, wherein said handheld medical device communicates wirelessly with said base unit, and in which wireless communication protocols used by said base unit and said handheld medical device comprise at least one of Bluetooth, IEEE 802.11a, IEEE 802.11b, IEEE 802.11g, any proprietary wireless communication layers in the Industrial, Scientific and Medical (ISM)-band, IrDA, Serial Ir, and any other optical protocol.

69. The apparatus of claim 56, wherein said electrical connection is a physical connection.

70. The apparatus of claim 56, wherein said electrical connection is a nonphysical connection.

71. The apparatus of claim 56, wherein said base unit comprises a cradle that receives the handheld medical device.

72. The apparatus of claim 56, wherein said base unit comprises a power cord, a port connection, and a network connection.

73. The apparatus of claim 56, wherein said base unit comprises a power cord which provides DC power to the base unit from AC line voltage.

74. The apparatus of claim 56, wherein said base unit comprises a port connection comprising at least one of a USB connection, a Firewire connection, serial connection, a parallel connection, and combinations thereof.

75. The apparatus of claim 56, wherein said base unit comprises an Ethernet network connection.

76. The apparatus of claim 56, further comprising an electronic device connected directly to the base unit and a remote station connected to the base unit over a network, wherein the handheld medical device is configured to received the update provided from at least one of the electronic device and the remote station.

77. The apparatus of claim 56, further comprising an electronic device connected directly to the base unit and a remote station connected to the base unit over a network, wherein the handheld medical device is configured to received the update provided from at least one of the electronic device and the remote station, and wherein the electronic device and the remote station are at least one of a computer, a laptop, a pager, a personal digital assistant, a computer server, a printer, a mobile phone, and any medical devices or electronic devices having an embedded microprocessor running software compatible with said the handheld medical device and base unit and in communication with the base unit.

78. The apparatus of claim 56, further comprising an electronic device connected directly to the base unit and a remote station connected to the base unit over a network, wherein the handheld medical device is configured to received the update provided from at least one of the electronic device and the remote station, and wherein said network is at least one of a public switched telephone network, a cellular telephone network, a local area network, a wide area network, a global computer network, an integrated services digital network, a dedicated security network, and a private building maintenance network.

79. The apparatus of claim 56, wherein said handheld medical device and said base unit communicate via a combination of wireless and physical communication links via said first and second communication interfaces.

80. The apparatus of claim 56, wherein said base unit comprises a cradle for supporting the handheld medical device, and wherein seating the handheld medical device in said cradle provides the electrical connection between battery terminals of the handheld medical device and the base unit for charging the battery of the handheld medical device.

81. The apparatus of claim 56 wherein the microcontroller which monitors and governs supplying power to a battery terminal from the power supply is configured to disconnect power should a fault condition in the power supply be detected by the microcontroller.

* * * * *

UNITED STATES PATENT AND TRADEMARK OFFICE
CERTIFICATE OF CORRECTION

| | | |
|---|---|---|
| PATENT NO. | : 8,770,482 B2 | Page 1 of 1 |
| APPLICATION NO. | : 11/411723 | |
| DATED | : July 8, 2014 | |
| INVENTOR(S) | : Friedrich Ackermann et al. | |

It is certified that error appears in the above-identified patent and that said Letters Patent is hereby corrected as shown below:

In The Claims
Col. No. 18, Line No. 36, Claim No. 57 "with said network though said" should read
--with said network through said--

Signed and Sealed this
Seventeenth Day of February, 2015

Michelle K. Lee
*Deputy Director of the United States Patent and Trademark Office*